United States Patent [19]

Lonardo

[11] Patent Number: 4,840,168

[45] Date of Patent: * Jun. 20, 1989

[54] COMBINATION ARM SPLINT AND FINGER SUPPORT MEANS

[76] Inventor: Robert Lonardo, 680 Capri Blvd., Treasure Island, Fla. 33706

[*] Notice: The portion of the term of this patent subsequent to Nov. 8, 2005 has been disclaimed.

[21] Appl. No.: 231,223

[22] Filed: Aug. 11, 1988

Related U.S. Application Data

[63] Continuation of Ser. No. 052,477, May 21, 1987, Pat. No. 4,782,825.

[51] Int. Cl.$^4$ ............................................. A61F 5/10
[52] U.S. Cl. ................................. 128/77; 128/87 A
[58] Field of Search .................. 128/77, 68, 87 A, 89, 128/165, DIG. 6, 87 R, DIG. 15

[56] References Cited

U.S. PATENT DOCUMENTS

| | | | |
|---|---|---|---|
| 2,312,523 | 3/1943 | Corbett | 128/87 A |
| 2,520,035 | 8/1950 | Goldberg | 128/87 A |
| 3,707,963 | 1/1973 | Keropian | 128/77 |
| 3,714,940 | 2/1973 | Palmer | 128/77 |
| 3,769,970 | 11/1973 | Swanson | 128/77 |
| 3,776,225 | 12/1973 | Lonardo | 128/77 |
| 4,366,812 | 1/1983 | Nuzzo | 128/77 |
| 4,384,571 | 5/1983 | Nuzzo et al. | 128/77 |

Primary Examiner—Paul T. Sewell
Assistant Examiner—Huong Q. Pham
Attorney, Agent, or Firm—Zarley, McKee, Thomte, Voorhees & Sease

[57] ABSTRACT

An arm splint is disclosed comprising upper and lower layers with a hand receiving portion formed on the forward end thereof. The rearward ends of the upper and lower layers are detachably secured together and are integrally secured together at the forward ends thereof through a fold that is created in the material of the device. Conventional retaining bands extend between the layers to conventionally hold the arm splint to the forearm of the patient.

A separate elongated slot is formed between the two layers adjacent the forward ends thereof to receive the support arm of a plurality of thumb and finger support means. Pin means is provided in an aperture extending through the slot member for detachably holding the support arms of the thumb and finger support means within said slot. Each of the support arms has one or more apertures for reception of the pin means.

8 Claims, 4 Drawing Sheets

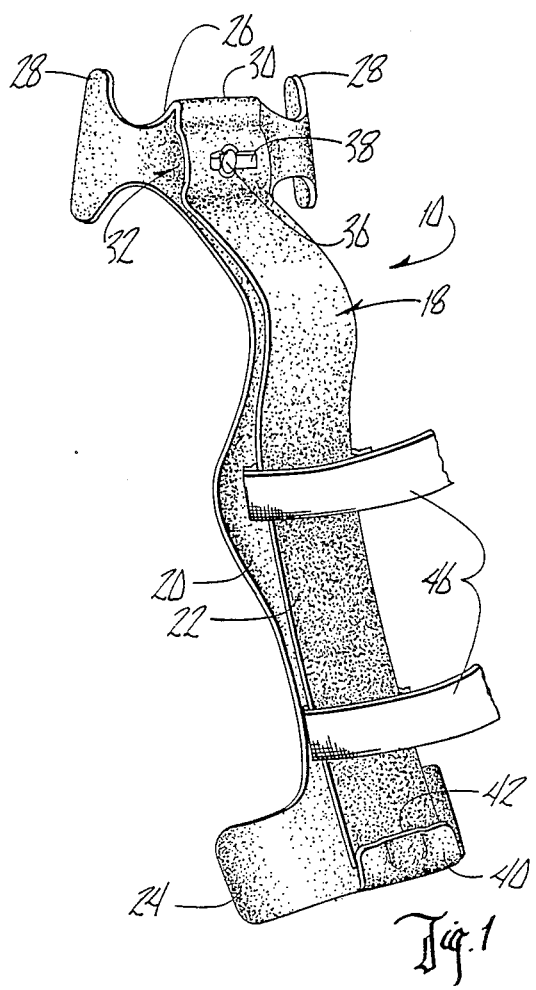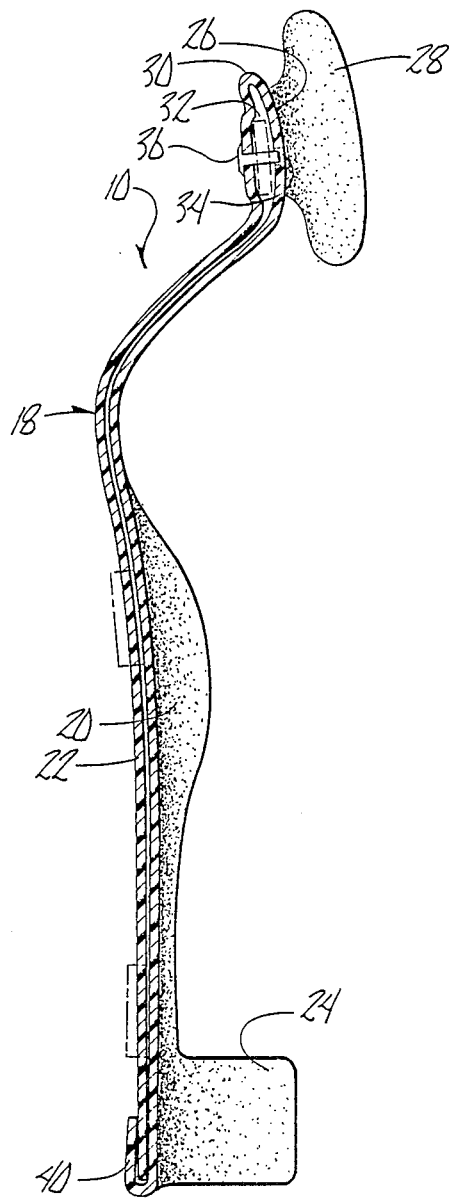

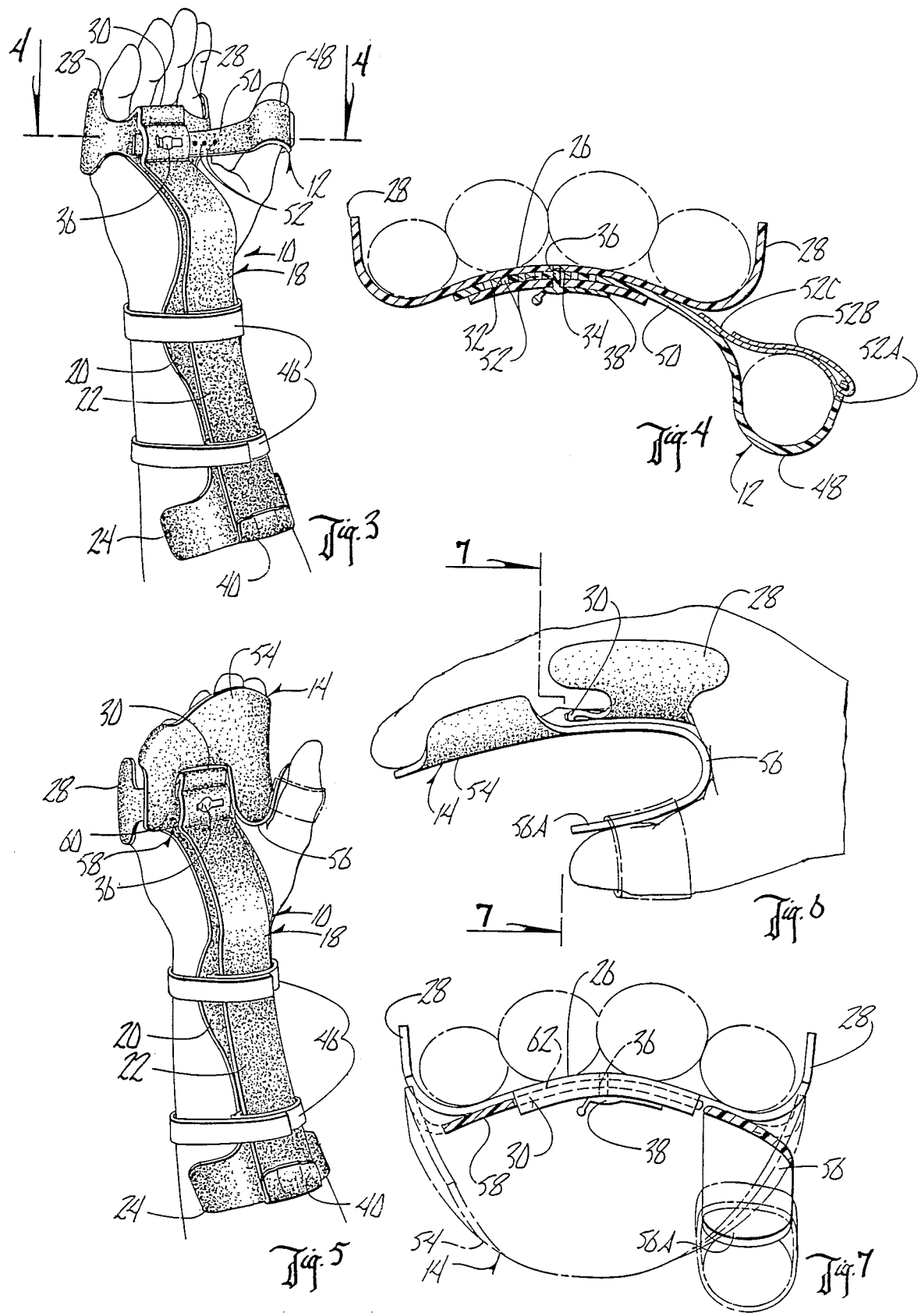

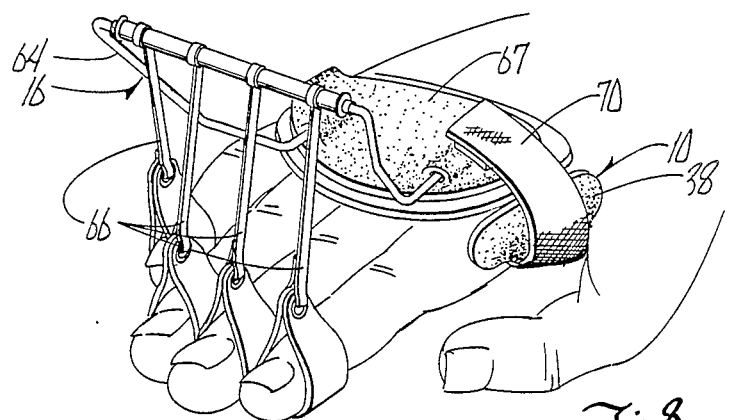
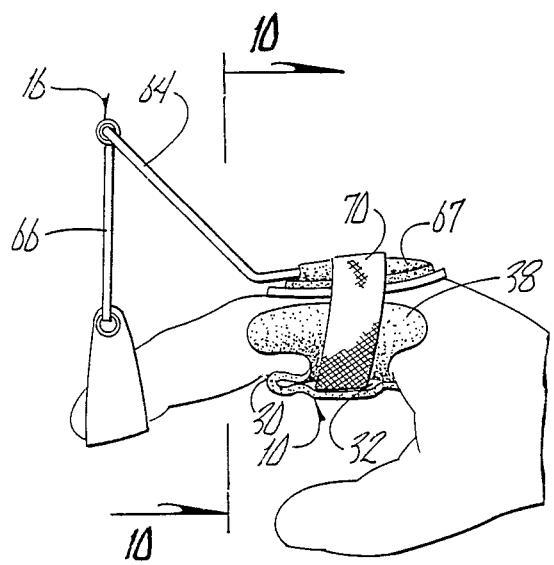
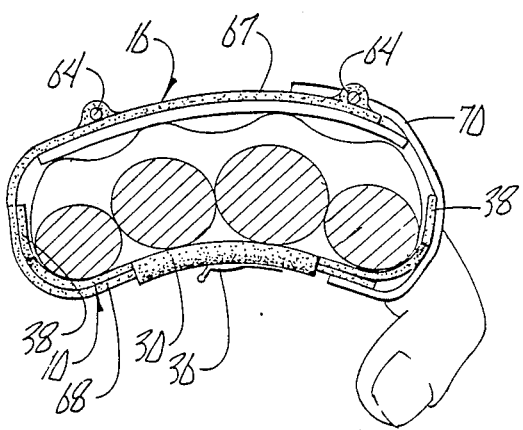

COMBINATION ARM SPLINT AND FINGER SUPPORT MEANS

This is a continuation of copending application Ser. No. 052,477, filed on May 21, 1987, now U.S. Pat. No. 4,782,825.

BACKGROUND OF THE INVENTION

Armsplints of the type shown in my prior U.S. Pat. No. 3,776,225 issued Dec. 4, 1973, have been useful in supporting and maintaining a patient's forearm in an immobile condition for such purposes of receiving and intravenous injection or the like. Other devices exist in the medical field to support a patient's fingers and/or thumb either collectively or individually for medical treatment. Each of these devices must be separately mounted on a patient's hand, and require individual base supports.

A principal object of this invention is to improve the arm splint of my previous patent by improving the interconnection between the strap bar with the splint to prevent any lateral movement of the strap bar when the device is in use.

A further object of this invention is to provide an arm splint which is adapted to receive various thumb and finger supporting mechanisms so that the arm splint can serve as the base support for a plurality of such mechanisms.

A further object of this invention is to provide an arm splint into which a plurality of different finger and thumb support mechanisms can be easily and quickly interchangeably inserted to serve the needs of different patients.

These and other objects will be apparent to those skilled in the art.

BRIEF SUMMARY OF THE INVENTION

An arm splint having upper and lower layers or bars has a hand receiving portion formed on the forward end thereof. The rearward ends of the upper and lower layers are detachably secured together, and are integrally secured together at the forward ends thereof through a fold that is created in the material of the device. Suitable conventional bands extend through the layers to conventionally hold the arm splint to the forearm of the patient.

A separate elongated slot is formed between the two layers adjacent the forward ends thereof to receive one of a plurality of thumb and finger support means. Each of these support means has a laterally extending support arm which extends into this slot. Means is provided in the slot member for detachably binding the support arm therein to prevent its movement while in use.

BRIEF DESCRIPTION OF THE DRAWINGS

FIG. 1 is a bottom perspective view of the arm splint of this invention;

FIG. 2 is an elongated sectional view thereof shown at an enlarged scale;

FIG. 3 is a perspective view similar to that of FIG. 1 wherein the splint is shown on the arm of a patient, and a thumb support means is mounted on the forward end of the arm splint;

FIG. 4 is a sectional view shown at an enlarged scale as taken on lines 4—4 of FIG. 3;

FIG. 5 is a view similar to that of FIG. 3 but wherein a finger and thumb support means is mounted on the forward end of the arm splint;

FIG. 6 is a side elevational view shown at an enlarged scale of the finger and thumb support mechanism of FIG. 5;

FIG. 7 is a sectional view taken on line 7—7 of FIG. 6;

FIG. 8 is a perspective view of a patient's hand mounted in an alternate form of a finger support mechanism;

FIG. 9 is a side elevation view of the device shown in FIG. 8;

FIG. 10 is a sectional view taken on line 10—10 of FIG. 9;

DESCRIPTION OF THE PREFERRED EMBODIMENT

Figure 11:
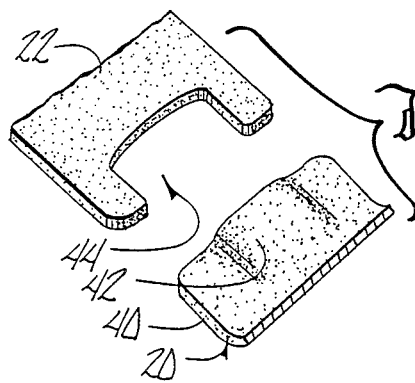
FIG. 11 is a partial exploded view of the innerlocking rearward ends of the upper and lower layers of the splint.

The numeral 10 designates the arm splint of this invention. The numeral 12 designates the thumb support that can be mounted thereon (see FIG. 13); the numeral 14 designates the finger and thumb support (see FIG. 12); and the numeral 16 designates the finger support (see FIG. 14).

The arm splint 10 is comprised of an elongated strip 18 which in turn is comprised of an upper layer 20 and a lower layer or bar 22. Conventional laterally extending support flanges 24 are secured to the rearward end of the upper layer 20 to engage the sides of the patient's forearm.

A hand support portion 26 is provided at the forward end of arm splint 10. Lateral extending support flanges 28 are formed at the sides of the hand support portion 26 to engage opposite sides of a patient's hands. A fold or hinge 30 at the forward end of the splint 10 joins the upper and lower layers 20 and 22, respectively. This fold is slightly flexible so as to permit the rearward ends of the layers to be disengaged as will be discussed hereafter.

As shown in FIGS. 1 and 2, a slot opening 32 appears between the upper and lower layers 20 and 22, respectively, adjacent the forward ends thereof. An aperture 34 extends through the slot opening as best seen in FIG. 2. A plastic pin 36 is adapted to extend through apertures 34 and slot opening 32 to affix certain support arm components therein as will be discussed hereafter. Pin 36 is attached to tab 38 (see FIG. 7) which in turn is fixedly secured to the lower layer 22. Tab 28 is of flexible material and serves only to retain pin 36 to the splint 10.

The rearward end of upper layer 20 terminates in a U-shaped portion 40 as best shown in FIG. 2. As shown in FIG. 11, a raised portion 42 is present in the U-shaped portion 40, and this raised portion nests in the notch 44 that is formed in the rearward end of the lower layer 22. The splint 10 is preferably comprised of the semi-rigid plastic material described in U.S. Pat. No. 3,776,225. The lower layer 22 can be moved laterally into and out of the U-shaped portion 40. When the notch 44 is embracing the raised portion 42, the upper and lower layers are prevented from moving side to side during normal use of the splint. These interlocking parts can be disengaged by manually forcing the rearward end of the lower layer laterally with respect to the U-shaped portion 40. The disengagement of these parts is sometimes desirable when conventional retaining straps 46 are attached to the splint.

The arm splint 10, as described above, is essentially the same as the arm splint described in U.S. Pat. No. 3,776,225 except for the interlocking connections between the rearward ends of the upper and lower layers as shown in FIG. 11, and except for the slot opening 32 which is the most important part of this invention.

Figure 13:
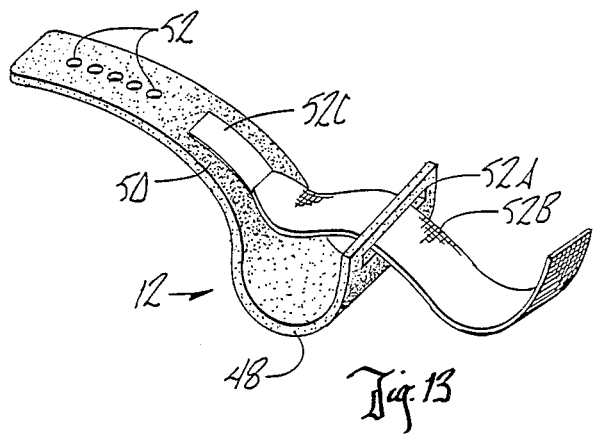
FIG. 13 is a perspective view of the thumb support.
Figure 14:
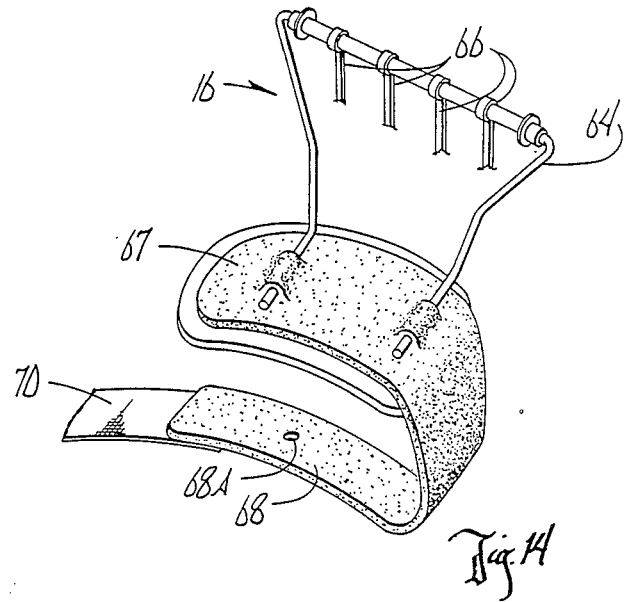
FIG. 14 is a perspective view of the finger support.

The thumb support 12, as best shown in FIG. 13, includes a U-shaped thumb support 48 with an arcuate support arm 50 extending laterally therefrom. A plurality of apertures 52 are located on the longitudinal axis of support arm 50 and are adapted individually to be in alignment with the aperture 34 so that when pin 36 extends through aperture 34 it will also extend through one of the apertures 52. This serves to hold thumb support 12 in a fixed position within the slot opening 32. A slot 52A is formed in one side of U-shaped thumb support 48 to receive a conventional fastening strap 52B which can function with the fastening strap 52C on arm 50 to securely fasten a patient's thumb within the member 48. The fastening straps 52B and 52C preferably use the Velcro system.

Figure 12:
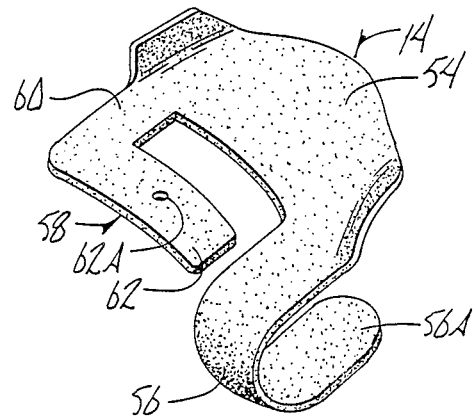
FIG. 12 is a perspective view of the finger and thumb support.

The finger and thumb support 14 is best shown in FIG. 12 and includes a finger support portion 54 which normally supports the four fingers of a patient's hand. An arcuate thumb support arm 56 extends rearwardly from the finger support portion 54 and terminates in a forwardly extending thumb support element 56A which is spaced from and underneath the finger support portion or base 54. A support arm 58 extends laterally from the portion 54. Arm 58 is L-shaped and is comprised of a first segment 60, a second segment 62 which extends laterally towards the thumb support arm 56. As seen in FIG. 12, the support arm 58 is spaced from both the portion 54 and the support arm 56, and dwells in substantially the same plane as the portion 54. Aperture 62A in segment 62 is adapted to receive pin 36 when support arm 56 is inserted into the aperture 34 of the slot opening 32 of the arm splint 10.

The finger support 16 (FIG. 14) includes a bracket 64 from which extend a plurality of conventional finger supports 66. The finger support 16 is in the shape of a horizontally disposed U with the bracket 64 being secured to the upper support arm 67 which is spaced from a lower support arm 68. The lower support arm 68 is adapted to be received in the slot opening 32 of the arm splint 10. Aperture 68A in arm 68 is adapted to receive the retaining pin 36 to hold the arm in rigid connection within the slot opening. A support strap 70 is affixed to the upper arm 67 and is adapted to extend around lateral support flanges 28 of the arm splint 10 to further support the finger support mechanism with respect to the arm splint. Again, conventional Velcro fasteners can be used in conjunction with support strap 70.

It should be emphasized that the finger and thumb support portions of the thumb support 12, the finger and thumb support 14, and the finger support 16 are all of conventional construction. The inventive aspect of each of these devices reflected in this application pertains to respective support arms that can be inserted into the slot opening 32 of arm splint 10 wherein the arm splint serves as the supporting mechanism for each of the attachments.

As reflected above, the support arms 50, 58 and 68 of thumb support 12, finger and thumb support 14, and finger support 16, respectively, can be selectively inserted into the slot opening 32 of the arm splint 10, and secured in position by the pin 36. As a result, each of the members 12, 14 and 16 does not need to be equipped with a special support means to affix it to the hand of the patient, thus adding to the utility of the arm splint 10.

Thus, it is seen that the device of this invention will achieve at least its stated objectives.

I claim:

1. In combination,
   a finger support,
   a forearm and wrist splint, comprising
   an elongated base strip having a longitudinal axis adapted to conform to the underside of a patient's forearm, said base strip having first and second layers, each having forward and rearward ends; said base strip being folded at its upper forward end and extending rearwardly with said second layer dwelling coextensively with said first layer,
   a hand support portion formed at said forward end of said first layer,
   connecting means detachably connecting the rearward ends of said first and second layers,
   a slot means formed between said first and second layers adjacent said forward ends, said slot means extending transversely with respect to the longitudinal axis of said base strip and being adapted to transversely slidably receive said finger support, and
   means for detachably securing said finger support within said slot means.

2. The combination of claim 1 wherein said connecting means is a U-shaped portion formed at said rearward end of said first layer that receives the rearward end of said second layer.

3. The combination of claim 1 wherein said finger support is adapted to support a plurality of fingers in an extended position, comprising a horizontally disposed U-shaped member having upper and lower support arms, bracket means secured to said upper arm and extending forwardly and outwardly therefrom, a plurality of finger support means on said bracket adapted for individual attachment to separate fingers of a patient's hand, said lower arm being adapted for insertion into said slot means.

4. The combination of claim 3 wherein said U-shaped member provides a space between said upper and lower arms to accommodate the thickness of a patient's hand.

5. The combination of claim 1 wherein said finger support comprises a U-shaped thumb support adapted to embrace the bottom and sides of a portion of a patient's thumb, said U-shaped thumb support having a support arm extending laterally therefrom and is adapted for insertion into said slot means.

6. The combination of claim 1 wherein said finger support comprises a finger support portion adapted to support the fingers of a patient's hand, an arcuate thumb support arm extending rearwardly from said finger support portion and terminating in a forwardly extending thumb support element spaced from and underneath said finger support portion, and a support arm extending laterally from said finger support portion and is adapted for insertion into said slot means.

7. The combination of claim 6 wherein said support arm is L-shaped and extends rearwardly and thence laterally toward said thumb support arm.

8. The combination of claim 2 wherein said U-shaped portion has a raised portion received in a notch formed in the rearward end of said second layer.

* * * * *